United States Patent [19]

Kitzinger et al.

[11] 4,096,437
[45] Jun. 20, 1978

[54] MAGNETIC TESTING DEVICE FOR DETECTING LOSS OF METALLIC AREA AND INTERNAL AND EXTERNAL DEFECTS IN ELONGATED OBJECTS

[75] Inventors: Frank Kitzinger, Montreal; Gregory A. Wint, Pierrefonds, both of Canada

[73] Assignee: Noranda Mines Limited, Toronto, Canada

[21] Appl. No.: 728,061

[22] Filed: Sep. 30, 1976

[30] Foreign Application Priority Data

May 6, 1976 Canada .................. 251932

[51] Int. Cl.² ........................... G01R 33/12
[52] U.S. Cl. ..................... 324/227; 324/235
[58] Field of Search .......................... 324/37

[56] References Cited

U.S. PATENT DOCUMENTS

| | | | |
|---|---|---|---|
| 3,271,664 | 9/1966 | Mountz et al. | 324/40 |
| 3,284,701 | 11/1966 | Kerbow | 324/37 |
| 3,315,154 | 4/1967 | Nuttall | 324/37 |
| 3,361,962 | 1/1968 | Albrecht | 324/41 |
| 3,424,976 | 1/1969 | Jezewski et al. | 324/37 |
| 3,443,211 | 5/1969 | Wood et al. | 324/37 |
| 3,529,236 | 9/1970 | Proctor | 324/37 |
| 3,843,923 | 10/1974 | De Vries et al. | 324/37 |

*Primary Examiner*—Robert J. Corcoran
*Attorney, Agent, or Firm*—Fleit & Jacobson

[57] ABSTRACT

A magnetic testing device for detecting defects in elongated objects is disclosed. The testing device comprises a permanent magnet assembly having poles adapted to be spaced apart in the longitudinal direction of an elongated object for inducing a longitudinal magnetic flux in a section of the object between the poles of the magnet assembly which is strong enough to saturate such section of the object, a tubular pole piece substantially centered on the elongated object adjacent each pole of the permanent magnet assembly for directing the magnetic flux radially into the object at one pole and out of the object at the other pole, Hall effect devices spaced around at least one pole piece in the path of the magnetic flux for sensing the radial flux entering into the elongated object, and means for sensing the variations of such magnetic flux as an indication of loss of metallic area in the object. The magnetic testing device is also provided with a leakage flux sensor located between the pole pieces for detecting external and internal defects in the object.

14 Claims, 12 Drawing Figures

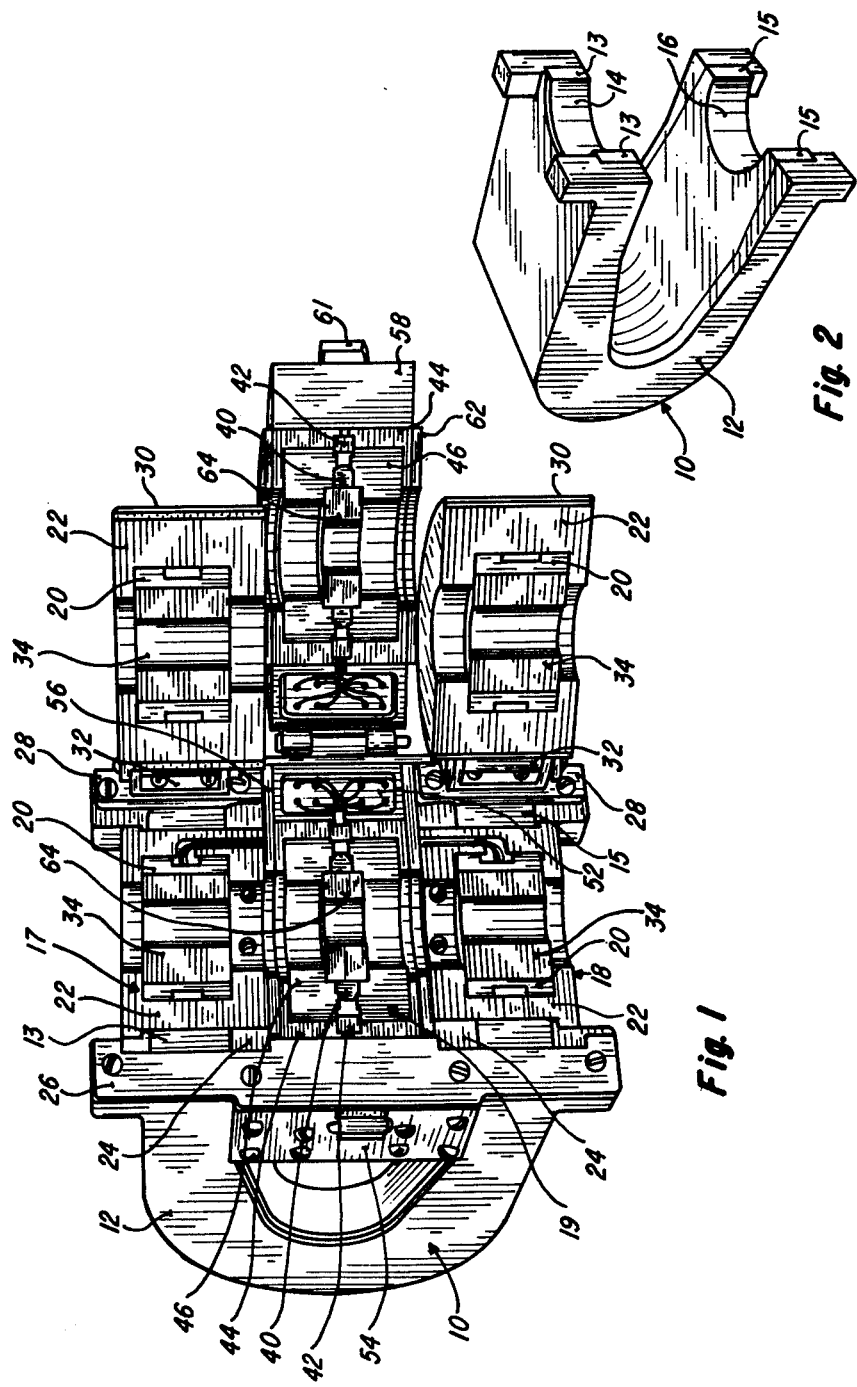

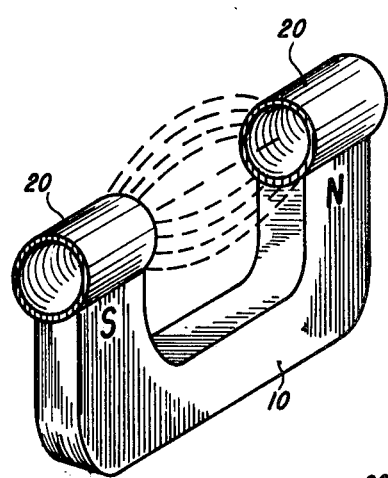
Fig. 7
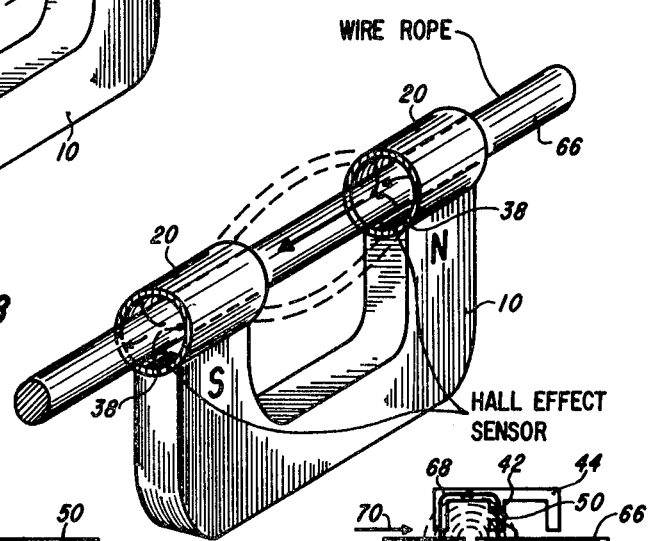
Fig. 8
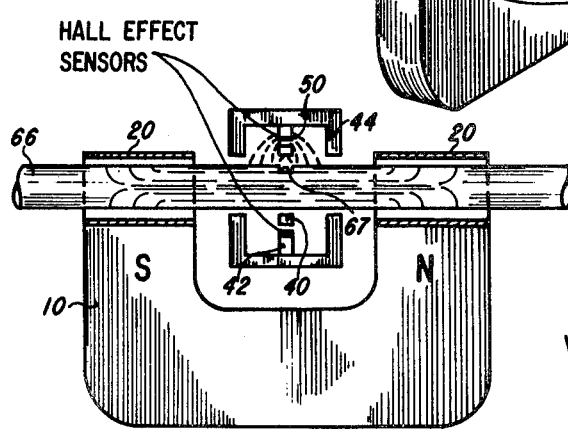
Fig. 9
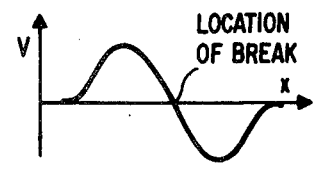
Fig. 10
Fig. 11

MAGNETIC TESTING DEVICE FOR DETECTING LOSS OF METALLIC AREA AND INTERNAL AND EXTERNAL DEFECTS IN ELONGATED OBJECTS

This invention relates to a magnetic testing device for detecting defects in elongated magnetically permeable objects, such as wire ropes, rods, steel pipes and similar magnetic objects.

Various magnetic devices have been proposed for detecting defects in wire ropes, steel pipes and other elongated magnetic objects. Such devices generally comprise electromagnets or permanent magnets for setting up a magnetic flux in the elongated object to be tested and means for detecting the leakage flux generated by the external and internal defects of such objects. An example of such devices is the one disclosed in U.S. Pat. No. 3,424,976 issued Jan. 28, 1969. These devices, however, are not well suited for detecting loss of metallic area due to wear, corrosion or other adverse conditions because these defects do not generally cause strong enough localized leakage flux.

It is therefore the object of the present invention to provide a magnetic testing device which is capable of adequately sensing loss of metallic area in elongated objects.

It is a further object of the present invention to provide a magnetic testing device which has the ability to detect loss of metallic area and, at the same time, other defects which cause a leakage flux in the elongated objects being tested.

The magnetic testing device, in accordance with the invention, comprises a permanent magnet assembly having poles adapted to be spaced apart in the longitudinal direction of the elongated object being tested for inducing a longitudinal magnetic flux in a section of such elongated object between the poles of the magnet assembly which is strong enough to saturate such section of the object, a tubular pole piece substantially centered on such elongated object adjacent each pole for directing the magnetic flux radially into the elongated object at one pole and out of the elongated object at the other pole, Hall effect devices spaced around at least one pole piece in the path of the magnetic flux for sensing the radial flux entering such elongated object, and means for sensing the variations in the magnetic flux as an indication of loss of metallic area in the elongated object.

Each tubular pole piece is preferably cut in two parts one of which is openable for positioning around the object to be tested.

The magnetic testing device preferably also includes a flux leakage sensor positioned between the poles of the magnet assembly for detecting external and internal defects which cause a leakage flux along the elongated object. The leakage flux sensor is magnetically shielded from the poles of the magnet assembly. Such leakage flux sensor may comprise a first sensor ring substantially centered on the elongated object, a second sensor ring concentrically mounted outside the first sensor ring and having a plurality of projections extending towards the first sensor ring with a minimum gap between the projections and the first sensor ring for concentrating the leakage flux through the gap, a Hall effect device located at each projection for sensing the leakage flux passing through the gap, and a flux guiding member connected to the first and second ring for completing the magnetic circuit of the leakage flux. The leakage flux sensor is preferably made in two parts one of which is openable for positioning the object to be tested.

The magnetic testing device preferably includes means for guiding the elongated object substantially along the center line of the pole pieces and leakage flux sensor. Such guiding means may be made of polyamide material.

The pole pieces are preferably separated from the poles of the permanent magnet assembly by a piece of strong non-magnetic and non-conductive material, such as linen base phenolic, for introducing a predetermined amount of reluctance in the magnetic circuit.

The invention will now be disclosed, by way of example, with reference to the accompanying drawings in which:

FIG. 1 illustrates a perspective view of the magnetic testing device in accordance with the invention;

FIG. 2 illustrates an embodiment of the permanent magnet used in the magnetic testing device in accordance with the invention;

FIGS. 7 to 11 show diagrams illustrating the operation of the testing device in accordance with the invention.

Figure 3:
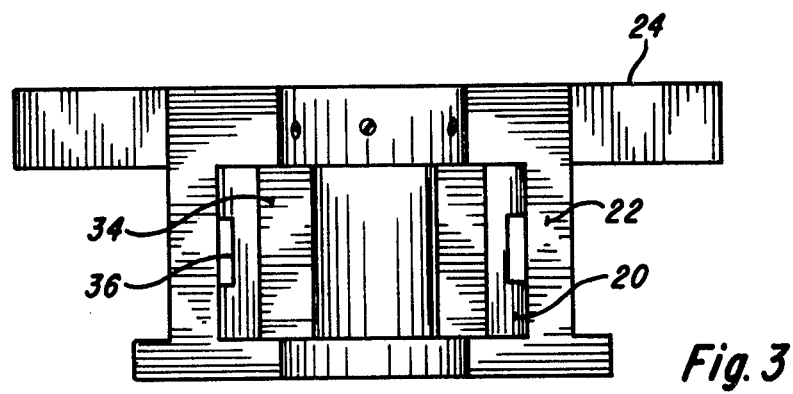
FIGS. 3 and 4 illustrate in more details the loss of metallic area sensor of the testing device of FIG. 1.

Referring to FIGS. 1 and 2, there is shown a perspective view of an embodiment of a magnetic testing device comprising a U shaped magnet assembly 10 which may be made of an aluminum-nickel-cobalt alloy which is enclosed in a zinc casting 12. The purpose of the casting is to provide a softer material for drilling holes to attach the other elements of the testing device. The permanent magnet itself is more clearly illustrated in FIG. 2 and includes two north poles 13 which are separated by a semi-circular section 14 and two south poles 15 which are also separated by a semi-circular section 16. Loss of metallic area sensors 17 and 18 are placed in the above semi-circular sections 14 and 16 respectively. A leakage flux sensor 19 is positioned between the north and south poles of the magnet.

Figure 4:
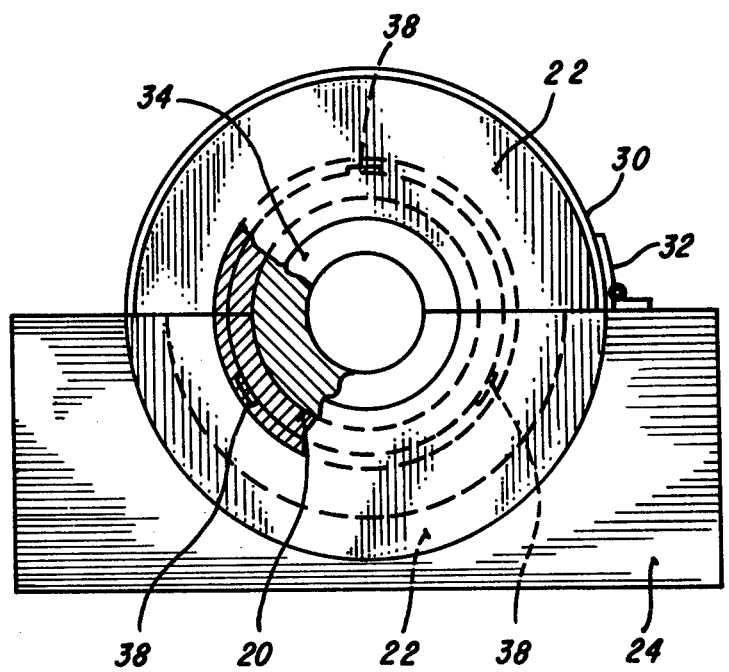

Sensors 17 and 18 are more clearly illustrated iin FIGS. 3 and 4. Each sensor is made in two parts one of which is fixed to the magnet and the other openable for positioning the object being tested. Each sensor half includes a semi-circular pole piece 20 which is secured inside a semi-circular member 22 of strong non-magnetic and non-conductive material, such as linen base phenolic. Each fixed member 22 is secured to a plate 24 itself secured to plates 26 and 28 which are in turn attached to magnet 10. Each openable member 22 is fixed on an outside semi-circular casing 30 which is hinged on plate 28 by hinge 32. Inside each pole piece 20 is secured a replaceable guide 34 for guiding the elongated object along the center axis of the pole piece 20. Such guides are made of hard plastic material such as polyamide. In groove 36 in pole pieces 20, there are regularly spaced Hall effect devices 38. Such devices are shown in FIG. 4 as being spaced about 120° apart. It is to be understood that the number and accordingly the spacing of such Hall effect devices may vary depending on the magnitude of the signal to be detected. The outputs of all the Hall effect devices are added up by means of a summing amplifier (not shown) to detect the loss of metallic area at any location on the perimeter of the elongated object and also for compensating for slight misalignment of the object with respect to the central axis of the pole pieces.

Figure 5:
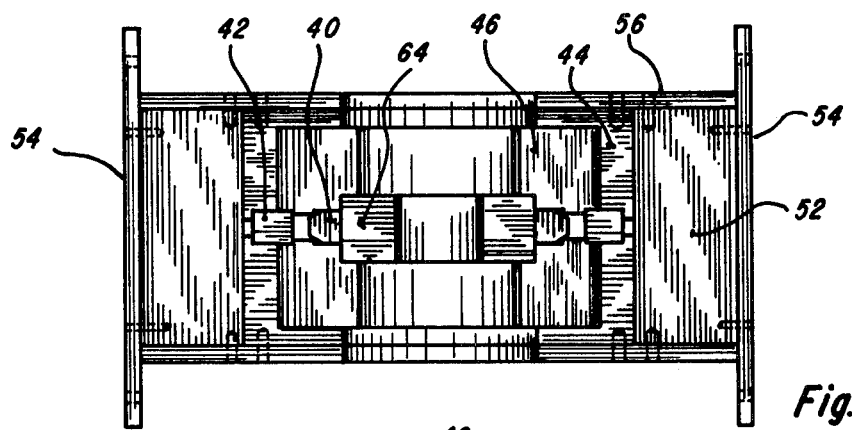
FIGS. 5 and 6 illustrate in more details the flux leakage sensor of the testing device of FIG. 1.
Figure 6:
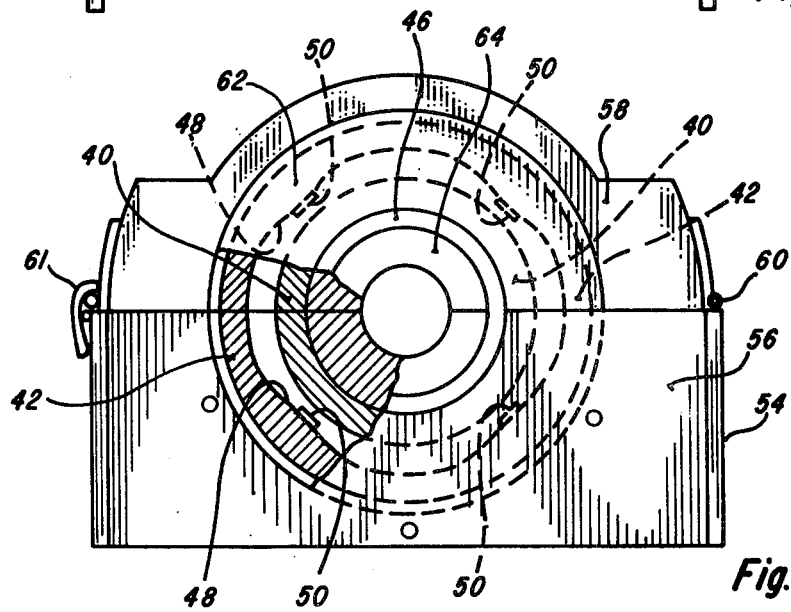

Sensor 19 is more clearly shown in FIGS. 5 and 6. Such sensor is made of two parts, one of which is fixed to the magnet 10 and the other openable for positioning the object to be tested. Each sensor half consists of a first semi-circular sensor ring 40, a second semi-circular sensor ring 42 concentrically mounted outside the first sensor ring, two flux guiding members 44 one on each side of the second semi-circular ring and a semi-circular block of strong non-magnetic and non-conductive material 46 secured inside each flux guiding member and holding the two sensor rings at a predetermined distance apart. As illustrated more clearly in FIG. 6, sensor ring 42 has a number of projections 48 thereon extending towards the first sensor ring 40 leaving a predetermined minimum gap between the projectings and the first sensor ring so as to concentrate the leakage flux through the gap. A Hall effect device 50 is located at each projection for detecting the leakage flux passing through the gaps. The fixed sensor half is supported between the poles of the magnet 10 by means of a block of hard non-magnetic and non-conductive material 52 which is secured to the magnet 10 by means of aluminum plates 54. The fixed sensor half is secured to aluminum plate 56 which is in turn fixed to block 52. Such plates are made of aluminum. The openable sensor half is secured to a block of strong non-magnetic and non-conductive material 58 which is hinged on the magnet by hinge 60 and secured in closed position by clamping device 61. A plate of aluminum 62 is secured to the outside portion of each openable guiding member 44. Semi-circular guides 64 are secured to the fixed and openable sensors to center the elongated object being tested. Such guide may be made of polyamide material.

The operation of the above disclosed magnetic testing device will now be disclosed with reference to the schematic diagrams illustrated in FIGS. 7 to 11 of the drawings. FIG. 7 illustrates the magnetic flux generated by magnet 10 in the absence of an elongated object within the pole pieces 20 whereas FIG. 8 illustrates the magnetic flux in the presence of an elongated object, such as wire rope 66. It will be seen that the major part of the flux goes radially from the north pole of the magnet into the wire rope, then longitudinally in the wire rope between the poles of the magnet, and radially out of the wire rope at the south pole of the magnet. Such flux thus passes through the Hall effect devices 38 which, as commonly known, produce an output voltage proportional to the flux passing perpendicularly through them. The magnitude of such voltage will depend on the reluctance of the magnetic circuit and thus on the gap between the magnet and the wire rope. Such gap will increase at the location of a loss of metallic area in the wire rope and reduce the flux passing through the wire rope. In addition, the reduced cross-section of the wire rope will also reduce the magnetic flux. The flux will be sensed at the output of the Hall effect devices. It is also very important to note that the amplitude of the output signal will be substantially independent of the speed at which the wire rope is passed through the magnet since Hall effect devices provide an output signal which is not influenced by the moving velocity of the test material within a wide range of velocities.

FIG. 9 illustrates the leakage flux generated due to the presence of a wire break 67. FIG. 10 illustrates the output voltage V of the Hall effect devices 50 as a function of the wire break position. Such output is null when the break is right under the Hall effect devices as the leakage flux passes longitudinally through the Hall effect devices. However, when the break is approaching or getting away from the location of the Hall effect devices, the magnetic leakage flux will pass at 90° through the Hall effect devices and the magnitude of the voltage detected will pass through maximum and minimum values. FIG. 11 shows the magnetic flux path 68 as the wire rope is moved through the leakage flux sensor in the direction of arrow 70.

Figure 12:
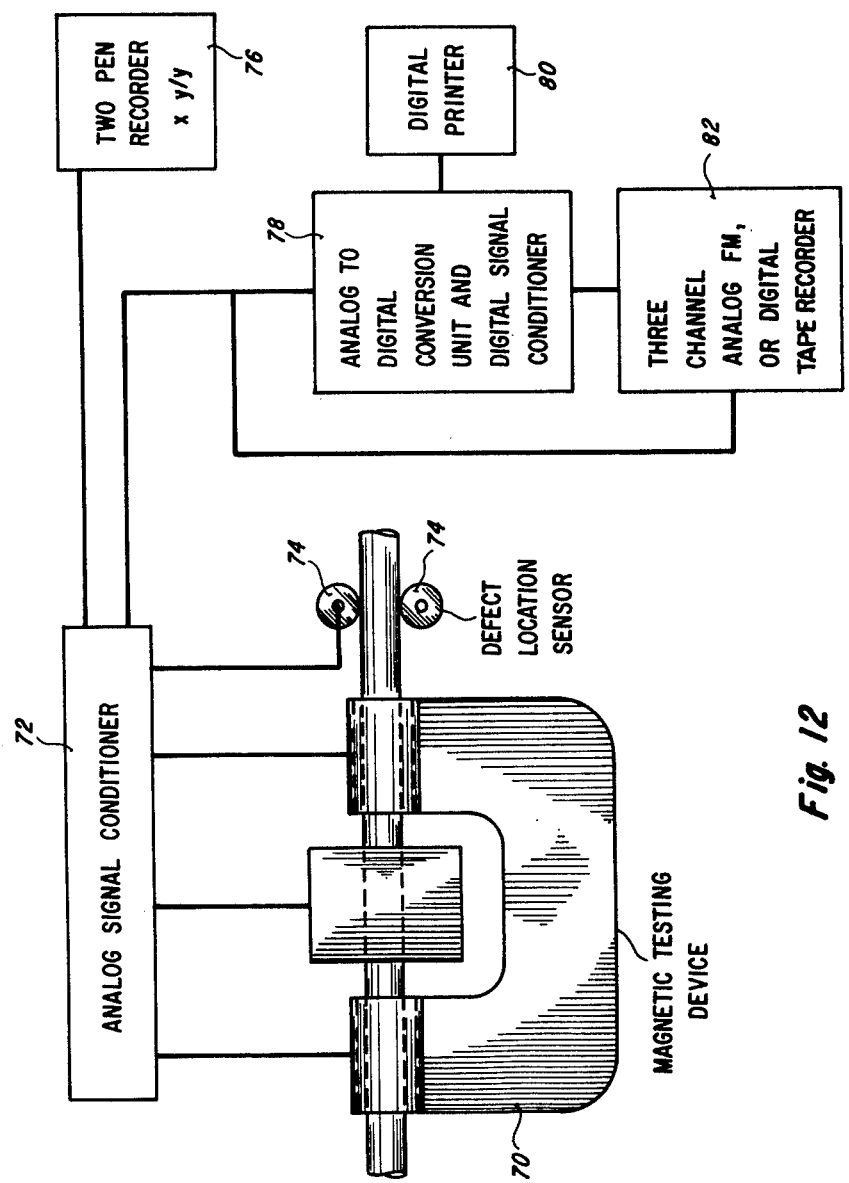
FIG. 12 illustrates a block diagram of the instrumentation used with the testing device in accordance with the invention.

FIG. 12 illustrates a block diagram of the instrumentation which may be used with the magnetic testing device in accordance with the invention. The Hall effect outputs of the magnetic testing device 70 are fed to an analog signal conditioner 72. Also fed to the analog signal conditioner is the output of a defect location sensor 74 which may be in the form of a pair of rollers in contact with the wire rope being tested. Such rollers may be provided with or coupled to suitable transducers producing an output signal at regular intervals from the starting end of the wire being tested. The output of the analog signal conditioner is fed to a two pen analog recorder x, y/y 76 providing, in a first trace, deflections giving an indication of wire breaks detected in the rope and in a second trace the loss of metallic area. The displacement of the recorder is proportional to the displacement of the wire. The output of the analog signal conditioner is also fed to an analog to digital conversion unit and digital signal conditioner 78 providing an output to a digital printer 80 for printing the type and location of the wire breaks and periodically the loss of metallic area. The outputs of conditioners 72 and 78 are also fed to a three channel analog FM or digital tape recorder 82 for recording the information detected by magnetic testing device 70.

It is also important to note that the above disclosed testing device facilitates the maintenance of a complete history of the wire rope being tested. Indeed, even if the wire rope wears out evenly, comparisons may be made with previous recordings to determine the loss of metallic area since the previous test.

Although the invention has been disclosed with reference to a preferred embodiment, it is to be understood that various other arrangements are also envisaged within the scope of the invention. For example, the permanent magnet may be any assembly capable of generating magnetic poles of opposite polarity along a section of an elongated object to be tested. Similarly, the detail structure of the loss of metallic area and leakage flux sensors could take various forms depending on the particular structure of the magnet assembly and on the shape of the objects to be tested.

What is claimed is:

1. A magnetic testing device for detecting loss of metallic area and internal and external defects in elongated magnetically permeable objects such as wire ropes and the like, the device comprising:
   (a) a permanent magnet assembly having poles adapted to be spaced apart in the longitudinal direction of an elongated object for inducing a longitudinal magnetic flux in a section of said object between the poles of the magnet assembly which is strong enough to saturate said section of the object;
   (b) a tubular pole piece adapted to surround said elongated object adjacent each pole of said permanent magnet assembly for directing said magnetic flux radially into the object at one pole and out of the object at the other pole;

(c) Hall effect devices spaced around at least one pole piece in the path of said magnetic flux for sensing the reduction of the radial flux entering said elongated object due to any reduction of the cross-sectional area of the elongated object between said pole pieces caused by loss of metallic area in said elongated object; and (d) a leakage flux sensor secured to said magnet between the pole pieces for detecting external and internal defects in said object.

2. A magnetic testing device as defined in claim 1, wherein each pole piece is separated in two parts, one of which is fixed to the magnet and the other hingedly mounted to the magnet for positioning along the object to be tested.

3. A magnetic testing device as defined in claim 1, wherein said leakage flux sensor includes a first sensor ring of magnetic material surrounding said elongated object, a second sensor ring of magnetic material concentrically mounted outside said first sensor ring and having the same axial length as the first sensor ring, said second sensor ring having a plurality of projections extending towards said first sensor ring with a predetermined minimum gap between said projections and said first sensor ring for concentrating the leakage flux through said gap, a Hall effect device located at each projection for detecting the leakage flux passing through said gap, and a flux guiding member of magnetic material surrounding said second ring and extending towards said elongated object for completing the magnetic circuit of said leakage flux.

4. A magnetic testing device as defined in claim 3, wherein said leakage flux sensor is in two parts, one of which is fixed to the magnet and the other hingedly mounted to the magnet for positioning the object to be tested.

5. A magnetic testing device as defined in claim 3, further comprising guiding means located within said leakage flux sensor and substantially centered on said elongated object for guiding said elongated object substantially along the center line of said pole pieces and leakage flux sensor.

6. A magnetic testing device as defined in claim 5, wherein said guiding means are polyamide guides.

7. A magnetic testing device as defined in claim 2, wherein said permanent magnet is a U-shaped magnet and wherein the legs of said magnet have semicircular sections into which are positioned each fixed pole piece.

8. A magnetic testing device as defined in claim 7, further comprising a tubular member of strong non-magnetic and non-conductive material separating said pole pieces from the poles of said magnet for providing a predetermined amount of reluctance in the magnetic circuit.

9. A magnetic testing device as defined in claim 8, wherein said material is a linen base phenolic material.

10. A magnetic testing device as defined in claim 3, further comprising means for mounting said first ring with respect to said second ring.

11. A magnetic testing device as defined in claim 10, wherein said means for mounting said first ring with respect to said second ring comprises a tubular member of non-magnetic material separating said first sensor ring from said second sensor ring and said flux guiding member.

12. A magnetic testing device as defined in claim 1, further comprising guiding means located within said tubular pole piece and substantially centered on said elongated object for guiding said elongated object substantially along the center line of said pole piece.

13. A magnetic testing device as defined in claim 1, further comprising means for adding the outputs of said Hall effect devices for compensating for slight misalignment of the object with respect to the center axis of the pole piece.

14. A magnetic testing device as defined in claim 13, wherein there are Hall effect devices spaced around both pole pieces.

* * * * *